United States Patent [19]

Desai

[11] Patent Number: 5,731,307
[45] Date of Patent: Mar. 24, 1998

[54] NEUROLEPTIC 2,7-DISUBTITUTED PERHYDRO-1H-PYRIDO[1, 2-A]PYRAZINES

[75] Inventor: Kishor A. Desai, Ledyard, Conn.

[73] Assignee: Pfizer, Inc., New York, N.Y.

[21] Appl. No.: 809,903

[22] PCT Filed: Aug. 21, 1995

[86] PCT No.: PCT/IB95/00670

§ 371 Date: Jun. 16, 1997

§ 102(e) Date: Jun. 16, 1997

[87] PCT Pub. No.: WO96/10570

PCT Pub. Date: Apr. 11, 1996

Related U.S. Application Data

[63] Continuation of Ser. No. 315,729, Sep. 30, 1994.
[51] Int. Cl.[6] .................... A61K 31/495; A61K 31/435; C07D 403/04; C07D 403/06
[52] U.S. Cl. .................... 514/217; 514/249; 544/349; 540/586; 540/592
[58] Field of Search .................... 514/217, 249; 544/349; 540/586, 592

[56] References Cited

U.S. PATENT DOCUMENTS

| | | |
|---|---|---|
| 5,109,002 | 4/1992 | Cain ..................... 514/256 |
| 5,122,525 | 6/1992 | Bright ..................... 514/249 |
| 5,157,034 | 10/1992 | Bright ..................... 514/249 |
| 5,185,449 | 2/1993 | Godek ..................... 546/272 |

FOREIGN PATENT DOCUMENTS

| | | |
|---|---|---|
| 380217 | 1/1990 | European Pat. Off. . |
| 9008144 | 7/1990 | WIPO . |
| 9213858 | 8/1992 | WIPO . |
| 9306101 | 4/1993 | WIPO . |
| 9325552 | 12/1993 | WIPO . |

OTHER PUBLICATIONS

B.R. de Costa et al., J. Med. Chem. 36, 2311–2320 (1993).
P. J. Gilligan et al., J. Med. Chem. 35, 4344–4361 (1992).
L. Cook, J. Pharm. Exp. Therap. 263(3), (159–1166 (1992).

*Primary Examiner*—Matthew V. Grumbling
*Attorney, Agent, or Firm*—Peter C. Richardson; Paul H. Ginsburg; Bryan C. Zielinski

[57] ABSTRACT

The instant invention is directed to compounds, compositions and antipsychotic methods of use wherein the compounds are of formula I:

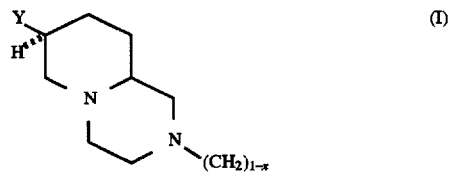

wherein Y is an imide or benzoyl alkyl group and X is a cycloalkyl, phenyl or dibenzoazepinyl group.

12 Claims, No Drawings

NEUROLEPTIC 2,7-DISUBTITUTED PERHYDRO-1H-PYRIDO[1, 2-A]PYRAZINES

This application claims priority under 35 U.S.C. § 371 from PCT/IB95/00670, filed Aug. 21, 1995, and is a continuation of Application No. 08/315,729, filed Sep. 30, 1994.

BACKGROUND OF THE INVENTION

The present invention is directed to certain 2,7- disubstituted perhydro-1H-pyrido[1,2-a]pyrazines which are depicted by the formula (I) as defined below, to pharmaceutical compositions comprising these compounds, and to a method of treating psychotic diseases therewith.

Sigma-receptor ligands have been widely studied and represent of a new class of potential antipsychotic drugs. From this viewpoint, a number of compounds which have a sigma-receptor antagonistic activity have been synthesized. Among these, compounds which have a piperdine or piperazine nucleus has been reported, for example, J. Med. Chem. 35, 4344, 1992; U.S. Pat. No. 4,956,368, U.S. Pat. No. 4,831,031, U.S. Pat. 4,957,916, U.S. Pat. 5,109,002; European Patent 503411-A1; and International Applications WO 92/14464-A1 and WO 93/09094-A1.

Compounds having the fused ring system of piperdine with piperazine also show sigma-receptor antagonistic activity.

U.S. Pat. No. 5,150,734, the disclosure of which is herein incorporated by reference, is directed to both racemic and optically active perhydro-1H-pyrido[1,2-a]pyrazines having the formula

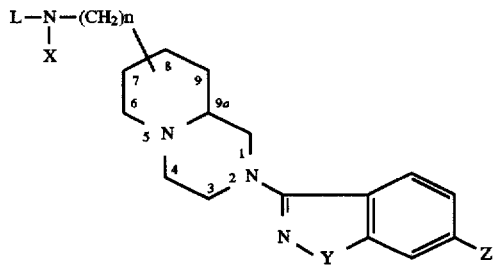

wherein
Z is H or Cl;
Y is O or S;
n is 1, 2, 3 or 4; and when
L and X are taken together are:

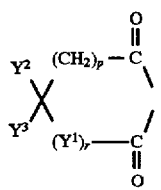

where $Y^1$ is $CH_2$, S, O or NH; $Y^2$ and $Y^3$ are taken separately and $Y^2$ and $Y^3$ are each independently hydrogen or methyl, or $Y^2$ and $Y^3$ are taken together and are $(CH_2)_q$; p is 1 or 2, q is 2, 3, 4 or 5; and r is 0 or 1.

Perhydro-1H-pyrido[1,2-a]-pyrazines of the following formula:

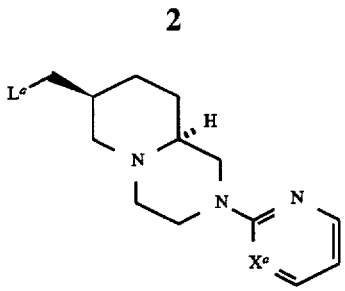

wherein $X^a$ is N or CH and $L^a$ represents one of certain pyrazolo, triazolo, tetrazolo or cyclic imido radicals have been reported to possess useful anxiolytic activity, Bright and Desai, International Application published under the PCT as WO 90/08144.

An NIH group reported that 2-(2-phenylethyl)perhydro-1H-pyrido[1,2-a]pyrazine has a potent sigma-receptor antagonistic activity (J. Med. Chem., 36, 2311, 1993).

In addition WO 93/06101 discloses a compound of the following formula,

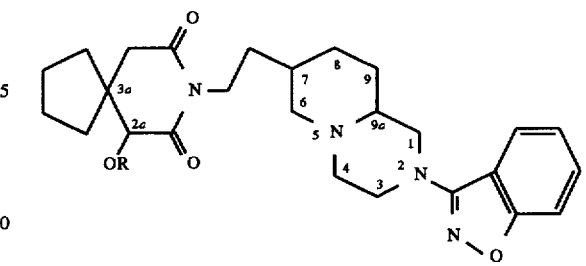

wherein R is hydrogen or $R^1C(=O)$, wherein $R^1$ is $(C_1-C_6)$ alkyl, phenyl, or phenyl substituted with one or two substituents selected from $(C_1-C_6)$alkyl, $(C_1-C_6)$alkoxy, halo, nitro and trifluoromethyl;
wherein the stereochemistry at the 2a position is R or S.

SUMMARY OF THE INVENTION

The present invention is directed to 2,7-disubstituted perhydro-1H-pyrido-[1,2-a]pyrazines having the formula

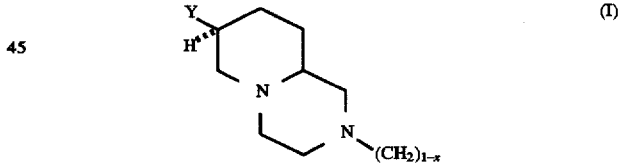

wherein
X is $C_3$–$C_6$ cycloalkyl, 5-(10,11-dihydro-5H-dibenz(b,f) azepinyl) or phenyl which may be substituted with one to three substituents selected from $C_1$–$C_6$ alkyl, $C_1$–$C_6$ alkoxy, halo, and halosubstituted $C_1$–$C_6$ alkyl;
Y is

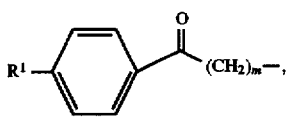

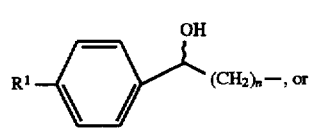

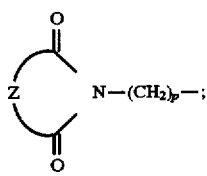

R[1] is hydrogen, $C_1-C_6$ alkyl, $C_1-C_6$ alkoxy, halo, or halosubstituted $C_1-C_6$ alkyl;

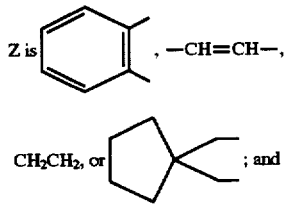

l, m, n and p are each, independently, an integer selected from 0 to 3;

with the proviso that if X is phenyl or substituted phenyl, l must be 1, 2 or 3; and optical isomers, stereoisomers and pharmaceutically acceptable salts thereof.

The compounds of formula I contain chiral centers and therefore exist in different enantiomeric and diastereomeric forms. This invention includes all such optical isomers and other stereoisomers of the compounds of formula I.

As used in this invention "alkyl" means straight or branched carbon chains of up to six carbon atoms.

"Substituted phenyl" means a phenyl ring having one to three substituents independently selected from $(C_1-C_6)$ alkyl, $(C_1-C_6)$ alkoxy, halo and halosubstituted alkyl.

"Halosubstituted alkyl" means alkyl substituted by one or more halogens, up to the maximum number of positions available for substitution.

In another aspect, this invention is directed toward a pharmaceutical composition for the treatment of psychotic disorders which comprises a neuroleptic effective amount of a compound of formula I or a pharmaceutically acceptable salt thereof and a pharmaceutically acceptable carrier.

In yet another aspect, this invention is directed toward a method of treating psychotic disorders which comprises administering to a psychotic patient in need of such treatment a neuroleptic effective amount of a compound of formula I or a pharmaceutically acceptable salt thereof.

Dependency-inducing agents such as cocaine and amphetamine have been shown to interact with sigma ligands. The compounds of the present invention are of value in prevention or reduction of dependence on these agents.

Preferred compounds of this invention are represented by formula I wherein X is cyclopropyl, or phenyl; Y is 4-fluorobenzoyl, (4-fluorophenyl)hydroxymethyl, or cyclopentanespiro-3'-glutamidomethyl; and l is 0, 1, or 2.

The more preferred compounds are:
trans-7-(p-fluorobenzoyl)-2-(cyclopropylmethyl) perhydro-1H-pyrido [1,2-a]pyrazine;
cis-7-(p-fluorobenzoyl)-2-(cyclopropylmethyl)perhydro-1H-pyrido [1,2-a]pyrazine;
trans-7-[2'-(p-fluorophenyl)-2'-hydroxyethyl]-2-(2-phenylethyl)perhydro-1H- pyrido[1,2-a]pyrazine; and
cis-7-(cyclopentanespiro-3'-glutamidomethyl)-2-(2-phenylethyl)perhydro-1H-pyrido [1,2-a]pyrazine.

In another aspect, this invention is directed to a racemic or optically active compound of the formula I or a pharmaceutically acceptable salt thereof which are useful intermediates for the preparation of compounds of formula I

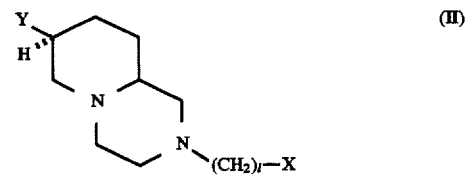

wherein

X is $C_3-C_6$ cycloalkyl, 5-(10,11-dihydro-5H-dibenz(b,f) azepinyl) or phenyl which may be independently substituted with one to three substituents selected from $C_1-C_6$ alkyl, $C_1-C_6$ alkoxy, halo, halosubstituted $C_1-C_6$ alkyl;

Y is $CH_2OH$, CHO, $CH_2CN$ or $CH_2OSO_2R$;

R is $C_1-C_3$ alkyl, phenyl or tolyl; and l is an integral selected from 0 to 3.

DETAILED DESCRIPTION OF THE INVENTION

Intermediates used in the preparation of the compounds of this invention are available from commerical sources, are known in the chemical literature or are described in U.S. Pat. No. 5,150,734, WO 93/06101 or WO 90/08144.

To obtain the compounds of the present invention, the following three routes are convenient.

The first route is described in method A. The starting material, alcohol (1), is oxidized by the Swern oxidation using $DMSO/COCl_2$ to the corresponding aldehyde (3). The aldehyde is reacted with the appropriate Grignard reagent, such as p-fluorophenylmagnesium bromide to give the secondary alcohol (4), which is followed by Swern oxidation to give the carbonyl compound (5).

METHOD A

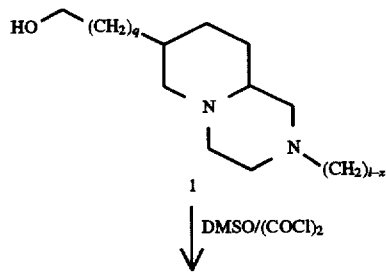

-continued
METHOD A

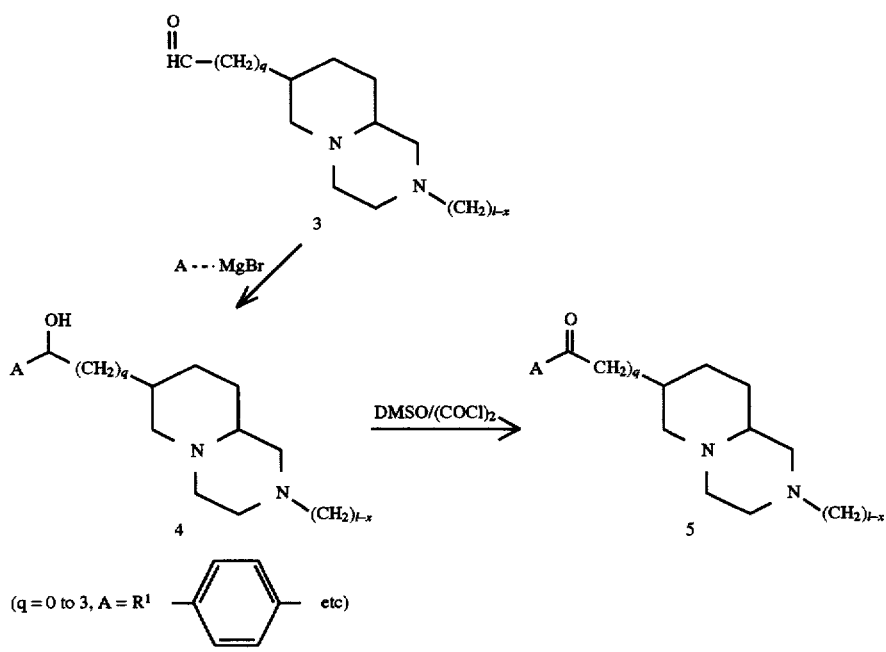

The second route is shown in method B. Thus the starting material (1) is converted to cyanocompound (7). At this step, if required, the hydroxy group is converted to a leaving group such as mesyl and then to the nitrile. Then the cyano compound is converted to an aldehyde (8), which gives secondary alcohol (9) and carbonyl compound (10) in a similar manner to Method A.

The third route is shown in method 0. Thus, the compound (6) in scheme B is directly reacted with an imide (11) such as phthalimide, succinimide, or cyclopentanespiro-3'-glutamide to give the desired compound (12).

METHOD B

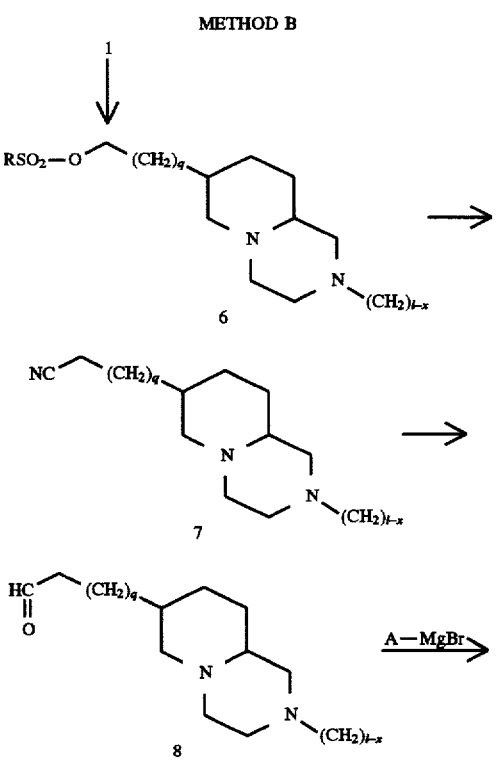

-continued

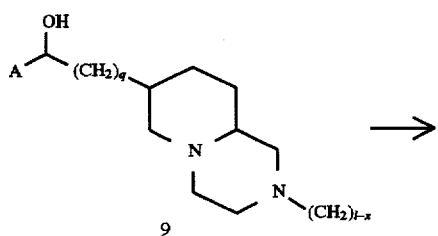

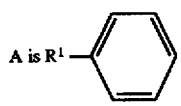

METHOD C

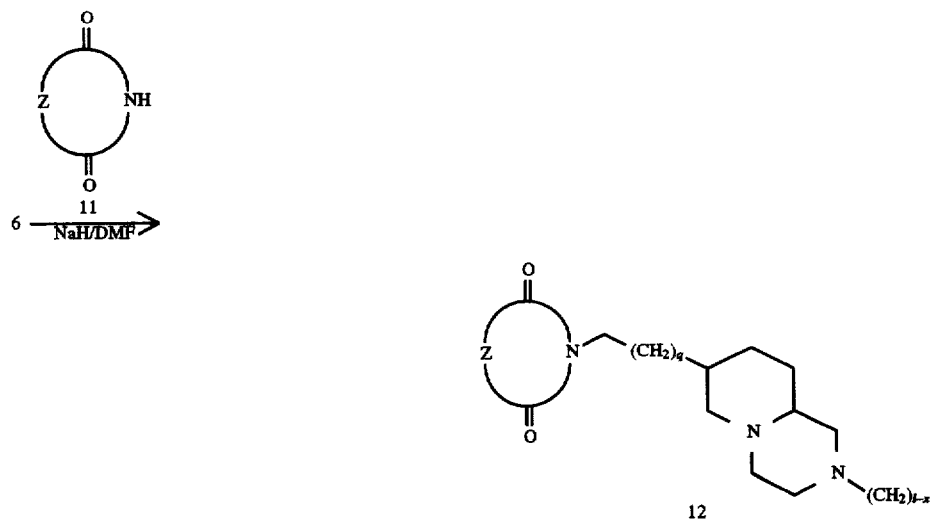

The reactions described above are carried out in a reaction inert solvent at room temperature to reflux temperature of the inert solvent, but if it is needed, a higher or lower temperature can be adopted. The reaction is easily monitored by TLC or HPLC. The reaction time is, in general, a few minutes to several hours. The resulting products are isolated and purified by standard methods which are well known to the chemist of ordinary skill.

The compounds of the formula I that are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

All clinically effective antipsychotic agents block dopamine binding to D-2 receptors, and demonstrate functional antagonism of dopamine-mediated behaviors in animals. Although the standard antipsychotics interact with a wide variety of neuro transmitter receptors, their potency in blocking D-2 binding is the only activity which shows a highly significant correlation with their oral clinical dosage (Creese et al., Science, 192:481–483, 1976). This clinical effect is believed to result from actions on mesolimbic-mesocortical dopamine projections to the forebrain, specifically inhibition of dopamine hypersensitivity caused by increased receptor density, as demonstrated in postmortem studies of schizophrenic brains (Lee et al., Nature, 274:897, 1978).

Affinity of compounds at the sigma binding site is determined by competition binding in rat whole brain homogenate against tritiated (+)propyl-3-(3-hydroxyphenyl) piperdine, (+)[3H]3PPP. The method is adapted from Largent et al. (1984) Proc. Natl. Acad. Sci. USA 81: 4983–4987. Whole brains of adult male Sprague-Dawley rats are removed after decapitation and homogenized in ice-cold 50 mM Tris.HCl buffer, pH 7.7 at room temperature, at 25 volumes per 1 gram. The suspension is centrifuged at 45000 g for 10 minutes, the supernatant discarded and the pellet resuspended in the same buffer at 25 volumes. This is repeated twice, with the final resuspension in 50 mM Tris.HCl, pH 8.0 at room temperature at 2 grams/100 ml. Assay tubes contain 50 ul of Vehicle (20% DMSO, 80% deionized water), Blank (10 μM (+−) Pentazocine), or test compound and 200 μl of (+)[3H]3PPP in Tris.HCl pH 7.7 buffer at 3.0 nM. 750 μl of tissue homogenate is added to each tube, vortexed, and incubated 90 min at 25° C. Samples are then rapidly filtered under vacuum through Whatman GF/B glass fiber filters presoaked for 90 min with 1.0% polyethyleneimine on a Brandel cell harvester and are washed with 2×5 ml cold 10 mM Tris.HCl, pH 7.7. Filters are removed and bound radioactivity counted in 20 ml scintillation vials with 15 ml Beckman Readysafe scintillation cocktail. Percent inhibition of specific binding by test compounds is used to calculated the $IC_{50}$, or extrapolated concentration of test drug necessary to inhibit one-half the total specific binding for each compound.

The biological activity of the compounds of this invention makes them useful for treating psychotic disorders in human subjects. For example, these compounds are useful for treating psychotic disorders of the schizophrenic types, and in particular the compounds are useful for removing or ameliorating such symptoms as anxiety, agitation, excessive aggression, tension and social or emotional withdrawal in psychotic patients.

A compound of formula (I), or a pharmaceutically-acceptable salt thereof, is administered to a human subject either alone, or preferably, in combination with a pharmaceutically-acceptable carrier or diluent, in a pharmaceutical composition, according to standard pharmaceutical practice. These compositions are administered orally or parenterally. Parenteral administration includes especially intravenous and intramuscular administration. Additionally, in a pharmaceutical composition comprising a compound of formula (I), or a pharmaceutically-acceptable salt thereof, the weight ratio of active ingredient to carrier will normally be in the range from 1:6 to 2:1, and preferably 1:4 to 1:1. However, in any given case, the ratio chosen will depend on such factors as the solubility of the active component, the dosage contemplated and the precise route of administration.

For oral use of the neuroleptic agents of this invention, the compounds are administered, for example, in the form of tablets or capsules, or as an aqueous solution or suspension. In the case of the tablets for oral use, carriers which can be used include lactose and cornstarch, and lubricating agents, such as magnesium stearate, can be added. For oral administration in capsule form, useful diluents are lactose and dried corn starch. When aqueous suspensions are required for oral use, the active ingredient can be combined with emulsifying and suspending agents. If desired, certain sweetening and/or flavoring agents can be added. For intramuscular and intravenous use, sterile solutions of the active ingredient can be prepared, and the pH of the solutions should be suitably adjusted and buffered. For intravenous use, the total concentration of solutes should be controlled to render the preparation isotonic.

When an agent of this invention is to be used in a human subject to treat a psychotic disorder, the daily dosage will normally be determined by the prescribing physician. Moreover, the dosage will vary according to the age, weight and response of the individual patient as well as the severity of the patient's symptoms. However, in most instances, an effective amount for treating a psychotic disorder will be a daily dosage in the range from about 1 to 500 mg, preferably about 5 to 100 mg, in single or divided doses, orally or parenterally. In some instances it may be necessary to use dosages outside these limits.

The following examples are provided for the purpose of further illustration and are not to be construed as limiting the scope of this invention in anyway. Nomenclature used herein is described in Rigaudy et al., IUPAC Nomenclature of Organic Chemistry, 1979 Edition, Pergamon Press, New York.

EXAMPLE 1

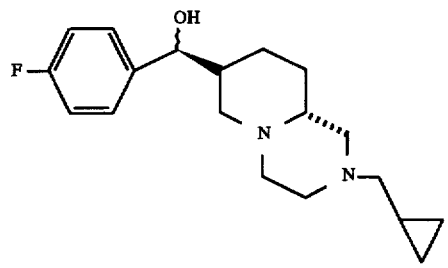

STEP 1

±Trans-7-hydroxymethyl-2-(cyclopropylmethyl) perhydro-1H-pyrido [1,2-a]pyrazine

To a solution of ±trans-7-hydroxymethyl-1H-pyrido [1,2-a]pyrazine (1.052 grams; 0.0058 moles) in DMF (10 mL), was added anhydrous sodium carbonate (1.57 g; 14.7 mm; 2.5 equivalent) and (bromomethyl)cyclopropane. (0.86 g;0.64 mm). The slurry was heated and stirred for four hours at 110° C. under an inert atmosphere. The reaction was allowed to cool to room temperature and concentrated to a solid mass. To this mixture was added 25 mL each of methylene chloride and water. The phases were separated and the aqueous phase was extracted with 25 mL of methylene chloride. The combined organic phases were dried over anhydrous sodium sulfate and concentrated to yield 0.763 g of oil (58.9%).

TLC:$R_f$=0.74 ($CH_2Cl_2$: MeOH:AQ.$NH_4$OH 6:1:0.1)

H.R.M.S.: 224.18715 (M+1; calc. 223.181)

$^{13}$CNMR ($CDCl_3$) delta; 8.039; 26.970; 29.297; 31.283; 36.364; 39.026; 52.899; 53.390; 54.767; 58.649; 59.129; 60.804; 63.497; 65.497.

STEP 2

±Trans-7-formyl-2-(cycloproplmethyl perhydro-1H-pyrido [1,2-a]pyrazine

To a flame dried 3 neck flask, attached to a bleach trap, was added methylene chloride (70 mL) and oxalyl chloride (2.98 mL; 41. mm). The solution was cooled to −78° C. and anhydrous dimethylsulfoxide (5.34 mL, 0.075 mole) was added dropwise as temperature exothermed to −50° C. The compound (from step 1; 8.4 g, 37.6 mm) was added to this solution, at −50° C. The mixture was stirred 1 hour at −45° C. (dry ice/acetonitrile bath). Triethylamine (20 mL, 143. mm) was added slowly followed by water (50 mL) at room temperature and the phases were separated. The aqueous phase was extracted four times with 50 mL of $CH_2Cl_2$. The organic phases were dried over anhydrous sodium sulfate and concentrated to yield 4.84 oil (58.1% yield).

TLC:$R_f$=0.49 (eluent: $CH_2Cl_2$; MeOH:AQ.$NH_4$OH 9:1:0.1)

NMR:$^1$HNMR ($CDCl_3$) delta; 9.60 (s,1H), 3.11–2.70 (m,5H), 2.62–2.55 (m, 1H), 2.40–2.30 (m,1H), 2.25–1.85 (m,5H), 1.8–1.7 (m,1H), 0.7–0.9 (m,1H), 0.51–0.45 (m,2H), 0.098–0.048 (m,2H).

STEP 3

±Trans-7-[1'-(p-fluorophenyl)-1'-hydroxymethyl]-2-(cyclopropylmethyl) perhydro-1H-pyrido[1,2-a]pyrazine To a solution of the aldehyde (3.84 g; 17.4 mm) from step 2 in 50 mL anhydrous THF was added, dropwise at −10° C., a 2 molar solution of p-fluorophenylmagnesium bromide in THF (9.55 mL, 19.1 mm). The solution was allowed to warm to room temperature and approximately 10 mL of ice water was added slowly followed by a 100 mL solution of saturated ammonium chloride solution; 200 mL of ether was then added with stirring and phases were separated. The organic phase was added over anhydrous sodium sulfate and concentrated to yield 2.69 grams of oil which was purified by flash column chromatography using 60 grams of silica gel (40 MM; Baker) and eluting with $CH_2Cl_2$: Methanol:28% AQ. ammonium hydroxide 12:1:0.04 380 mgs of solid was obtained (6.8% yield).

TLC: $R_f$=0.59 ($CH_2Cl_2$: MeOH:AQ.$NH_4$OH 9:1:0.1

H.R.M.S.: $M^+$ 318.21157 (calc.318.21)

$^{13}$CNMR ($CDCl_3$) delta: 8.071, 26.568, 27.077, 43.404, 43.472, 52.913, 52.982, 54.765, 57.908, 59.137, 60.497, 60.605, 63.572, 114.952, 115.231, 128.114, 128.221, 139.509, 160.505, 163.765.

EXAMPLE 2

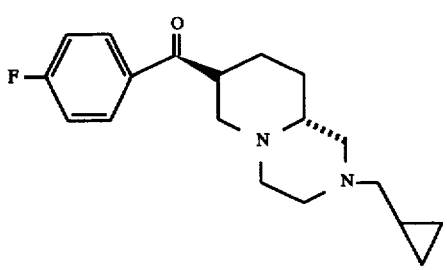

±Trans-7-(p-fluorobenzoyl)-2-(cyclopropylmethyl) perhydro-1H-pyrido[1,2-a]pyrazine The amino alcohol (300 mg; 0.99 mm) obtained from Example 1, Step 3 was converted to the ketone by employing the procedure as outlined for Example 1, Step 2. 159 mg solid was obtained which was purified by flash column chromatography using 10 grams of silica gel and eluting with $CH_2Cl_2$;$CH_2OH$:AQ.$NH_4$OH 18:1:04. Yield 63 mg white solid (21.14% yield).

TLC: $R_f$0.7($CH_2Cl_2$:$CH_2OH$:AQ.$NH_4$OH 9:1:01)

H.R.M.S.: $M^+$ 316.18150 (calc. 316.42)

$^{13}$CNMR ($CDCl_3$) delta: 8.235, 27.389, 29.245, 44.460, 53.133, 54.783, 57.137, 59.309, 60.428, 63.661, 115.637, 115.930, 130.850, 130.972, 132.377, 164.023, 167.402, 200.119.

Anal. calcd. for $C_{19}H_{25}N_2$ of: C 71.89%, H 8.26%, N 8.83%. Found C 71.81%, H 8.11%, N 8.59%.

EXAMPLE 3

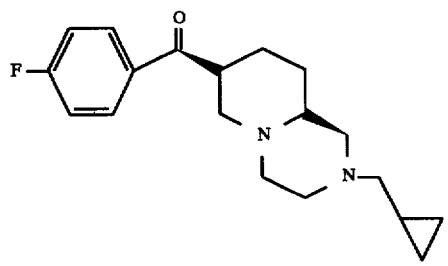

±cis-7-[P-fluorobenzoyl)-2-(cyclopropylmethyl) perhydro-1H-pyrido[1,2-a]pyrazine was synthesized by using a procedure analogous to the procedure described for the compound of Example 2.

TLC: $R_f$0.47(EtOAc:Hexane:MeOH:AQ.$NH_4$OH 1:1:015:0.03)

H.R.M.S.: $M^+$ 316.19563 (calc. 316.42)

$^{13}$CNMR ($CDCl_3$) delta: 8.023, 27.331, 29.187, 44.391, 53.072, 54.733, 57.100, 59.259, 60.369, 63.590, 115.554, 115.856, 130.791,130.913, 130.33, 163.394, 167.816.

EXAMPLE 4

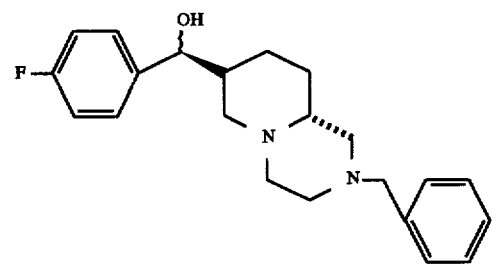

The compound of Example 4 was prepared by a method analogous to the method of Example 1 using benzyl chloride in place of bromomethylcyclopropane.

H.R.M.S.: 354.21299 (calc 352.194)

TLC: $R_f$=0.48 (EtOAc:Hexane:Methanol:AQ.$NH_4$OH 1:1:0.1:0.01)

$^1$H NMR ($CDCl_3$) delta: 7.28–7.17 (m,1H), 7.01–6.96 (m,2H), 4.26–4.22 (m,1H), 3.45–3.38 (m,2H), 3.13–2.42 (m,5H), 2.34–2.10 (m,4H), 1.90–1.69 (m, 4H), 1.65–1.37 (m,2H).

EXAMPLE 5

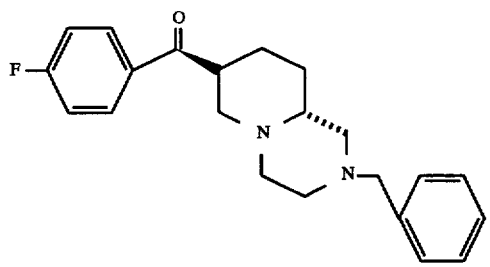

±Trans-7-(p-fluorobenzoyl)-2-(benzyl)-perhydro-1H-pyrido [1,2-a]pyrazine was synthesized by a method analogous to the method of Example 1.

Yield: 30.15%

H.R.M.S.: 352.19490 (calc. 351.186)

TLC: R$_f$=0.84 (CH$_2$Cl$_2$:MeOH:AQ.NH$_4$OH 9:1:0.1)

$^{13}$CNMR: (CDCl$_3$) delta: 27.392, 29.124, 44.476, 53.045, 54.857, 57.133, 59.063, 60.560, 62.990, 115.654, 115.951,127.076, 128.241,129.143, 130.880, 131.001, 132.393, 132.393, 132.427, 137.939, 164.051, 167.424, 200.141.

EXAMPLE 6

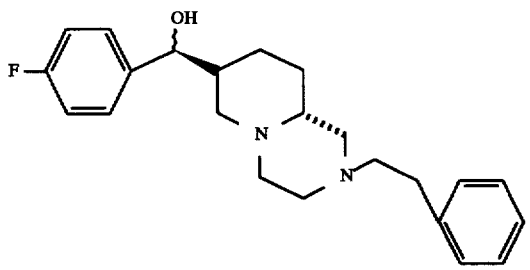

The compound of Example 6 was synthesized from the compound of Example 4. Treatment of the compound of Example 4 with palladium on carbon and hydrogen yielded the secondary amine which, upon alkylation with phenethyl bromide (Example 1), yielded the title compound.

Yield: 17.3% (overall yield, 2 steps)

H.R.M.S.: 368.22445 (calc 368.226)

TLC: R$_f$=0.6(CH$_2$Cl$_2$:MeOH:AQ.NH$_4$OH 9:1:0.1)

$^{13}$CNMR (CDCl$_3$) delta: 7.35–7.15 (m,4H), 7.10–6.95 (m,2H), 4.3–4.2 (m,1H), 2.85–2.6 (m,4H), 2.55–2.40 (m,2H), 2.35–2.0 (m,3H), 1.95–1.65 (m, 4H), 1.62–1.42 (m,1H), 1.4–0.95 (m,4H).

EXAMPLE 7

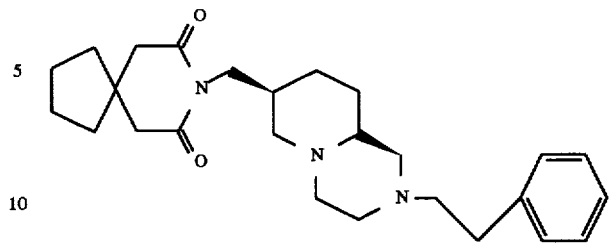

STEP 1

±cis-7-hydroxymethyl-2-(phenethyl)-perhydro-1H-pyrido-[1,2-a]pyrazine

The title compound was synthesized by a procedure similar to Example 1, Step 1 using bromomethyl benzyne in the place of bromomethylcyclopropane.

Yield: 80.8%

TLC: R$_f$=0.66 (CH$_2$Cl$_2$: MeOH:AQ.NH$_4$OH 9:1:0.1)

$^{13}$CNMR: (CDCl$_3$): 26.820, 27.301, 33.515, 34.251, 53.143, 54.956, 58.107, 59.331, 60.354, 60.889, 67.747, 126.042, 128.379, 128.669, 140.197.

STEP 2A

The compound of Step 1 (8.1 mm) was dissolved in 15 ml methylene chloride containing triethylamine (9.7 mm). The resulting solution was added dropwise at 0° C. to a solution of methane sulfonyl chloride (8.5 mm) in methylene chloride (7 ml). The resulting solution was stirred for 1 hour; warmed to room temperature and treated with water at pH 9.5 (NaOH). The phases were separated and the aqueous phase extracted with methylene chloride (30 ml). The combined organic phases were dried over sodium sulfate and concentrated to yield the methanesulfonate intermediate which was used in Step 2B without further purification.

STEP 2B

±cis-7-cyclopentanespiro-3'-glutarimidomethyl perhydro-1H-pyrido-[1,2-a]pyrazine.

To a flame dried flask, under inert atmosphere, were added anhydrous dimethylformamide (15 mL), 60% suspension of sodium hydride in oil (0.122 grams; 1.31 mm), and 3,3-pentamethyleneglutarimide (0.316 grams; 1.9 mm). The solution was heated and maintained at 45° C. for 2 hours. The reaction was cooled to room temperature and to it was added 0.632 grams (1.8 mm) of the title compound from step 2A of this procedure. The reaction was heated and maintained at 110° C. for 16 hours. It was cooled to room temperature and the solvent was removed in vacuo to solid. To this solid was added ethyl acetate (40 mL) and water (40 mL); the pH of the medium was adjusted to 2.2 with 1N aqueous hydrochloric acid and the phases were separated. Ethyl acetate (40 mL) was added to the aqueous phase and the pH was adjusted to 10.0 with 2N aqueous sodium hydroxide solution. The phases were separated, and the organic phase was dried over anhydrous sodium sulfate and concentrated to yield a solid. The product was purified by flash column chromatography using 10 grams of silica gel, eluting with CH$_2$Cl$_2$: MeOH:AQ.NH$_4$OH 12:1:0.04.

Yield: 220 mgs (28.9% yield)

TLC: R$_f$=0.68 (EtOAc:MeOH:AQ.NH$_4$OH 8.5:1:0.1)

H.R.M.S.: 423-28447 (calc. 423.288)

13CNMR: (CDCl₃): 24.254, 25.126, 25.226, 32.945, 33.531, 37.589, 39.371, 41.600, 45.031, 53.194, 55.062, 58.405, 59.318, 60.562, 61.193, 125.961, 128.342, 128.689, 140.404, 172.425.

Using the above general procedure, compounds shown below were synthesized.

EXAMPLE 8

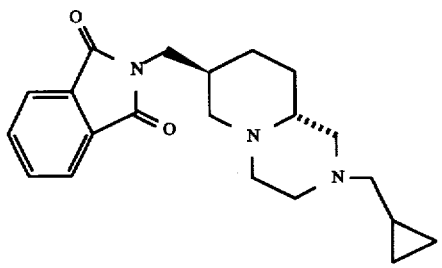

The compound of this Example was synthesized by a method analogous to the method of Example 7.

TLC: R$_f$=0.34 (CH$_2$Cl$_2$:MeOH:9:1)

Yield: 31.2%

13CNMR: (CDCl₃): 28.113, 28.377, 29.343, 36.329, 41.574, 53.028, 54.721, 59.033, 59.213, 60.427, 63.573, 123.288, 131.928, 133.995, 168.426

H.R.M.S. (calc. 353.21)

EXAMPLE 9

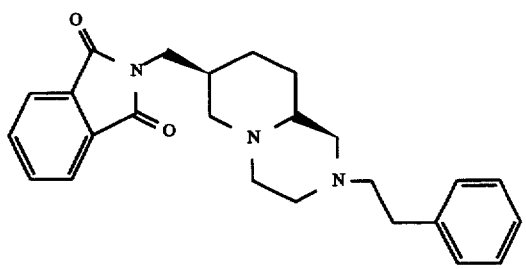

The compound of this Example was synthesized by a method analogous to the method of Example 7.

TLC: R$_f$=0.38 (CH$_2$Cl$_2$: MeOH:9:1)

Yield: 37.3%

13CNMR: (CDCl₃): 24.879, 32.977, 33.204, 39.941, 53.098, 54.595, 57.567, 59.069, 60.358, 60.722, 123.170, 126.144, 128.443, 128.714, 132.150, 133.868, 139.5; 168.652

H.R.M.S.M⁺ 403.19985 (calc.403.226)

EXAMPLE 10

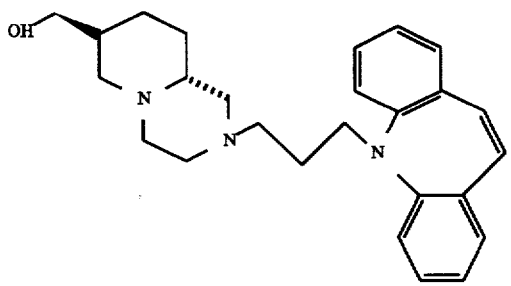

STEP 1

The title compound was synthesized by a procedure analogous to the procedure of Step 1, Example 1.

Yield: 4.3%

TLC: R$_f$=0.1 EtOAc:Hexane 1:4

13CNMR: (CD₃OD) delta: 31.421, 48.224, 61.070, 121.476, 124.409, 129.962, 130.146, 133.155, 133.339, 152.249.

STEP 2

The title compound from Step 1 was converted to its methylsulfonate derivative by a procedure analogous to Step 2A of Example 7 in 84.5% yield (TLC: R$_f$=0.79; CH$_2$Cl$_2$: MeOHJ 9:1).

STEP 3

±trans-7-hydroxymethyl-2[3-{5-(dibenz(b,f)-azepinyl}propyl]perhydro-1H-pyrido [1-2a]pyrazine A solution of the methanesulfonyl derivative from Step 2 (0.223 grams, 0.68 mm), dimethyl formamide (2.5 mL), ±trans-7-hydroxymethyl-perhydro-1H-pyrido[1-2a] pyrazine (0.463 grams, 2.7 mm) and sodium carbonate (0.18 grams, 1.7 mm) was stirred at 110° C. for 20 hours. It was allowed to cool to R. T. and DMF was removed in vacuo. The product was purified by column chromatography using silica gel (20 grams). Eluent: CH$_2$Cl$_2$: MeOH:A2.NM$_4$OH (12:1:0.04).

Yield: 0.22 grams (80% yield)

H.R.M.S.: 404-26902 (calc. 403.572)

TLC: R$_f$=0.17 (CH$_2$Cl$_2$: MeOH:AQ.NH$_4$OH 9:1:0.1)

13CNMR: (CDCl₃): 24.699, 26.851, 29.167, 39.053, 48.687, 52.949, 54.809, 56.024, 58.466, 59.122, 60.901, 66.031,120.408, 123.272, 128.809, 129.155, 132.138, 133.960, 150.827.

EXAMPLE 11

±trans-7-hydroxymethyl-2[3-{5-(10,11-dihydro-dibenz (b,f)-azepinyl)}propyl]perhydro-1H-pyrido[1-2a]pyrazine

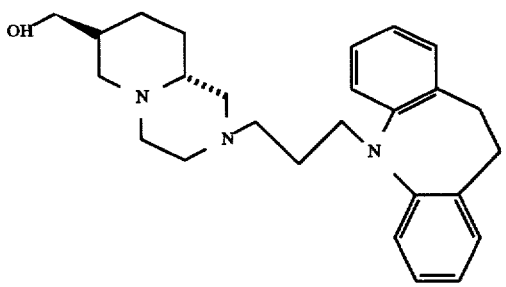

A solution of the title product from Example 10, Step 3 (107 mg; 0.27 mm) in ethanol (25 mL) and 10% Pd/C (34 mg), ethyl acetate (1 mL) was hydrogenated at 50 psi for 20 hours. The suspension was filtered over Celite® and solvent removed in vacuo to yield 108 mgs solid (100% yield).

Mass spec. 406 (calc. 405.27)

TLC: $R_f$=0.38 ($CH_2Cl_2$: MeOH 93:3)

$^{13}$CNMR: ($CDCl_3$) delta: 22.335, 23.813, 25.785, 27.365, 32.152, 37.341, 48.153, 50.420, 52.618, 55.121, 55.866, 67.179, 60.320, 64.704, 119.785, 112.697, 126.445, 129.920, 134.203, 147.905.

I claim:

1. A compound of formula (I)

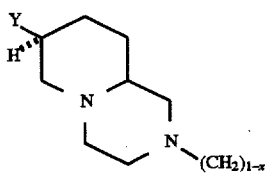

(I)

wherein

X is $C_3$–$C_6$ cycloalkyl, 5-(10,11-dihydro-5H-dibenz(b,f) azepinyl) or phenyl each of which may be substituted with one to three substituents independently selected from $C_1$–$C_6$ alkyl, $C_1$–$C_6$ alkoxy, halo, halosubstituted $C_1$–$C_6$ alkyl;

Y is

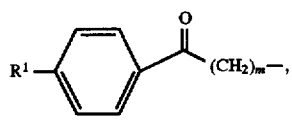

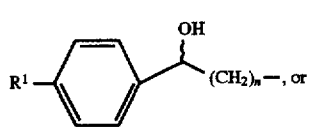

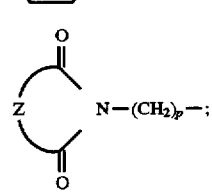

$R^1$ is hydrogen, $C_1$–$C_6$ alkyl, $C_1$–$C_6$ alkoxy, halo, or halosubstituted alkyl;

Z is 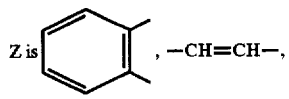, —CH=CH—,

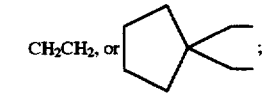

$CH_2CH_2$, or l,m,n and p are, each independently, an integer selected from 0 to 3; with the proviso that if X is phenyl or substituted phenyl, l must be 1, 2 or 3; and optical isomers, stereoisomers and pharmaceutically acceptable salts thereof.

2. A compound according to the claim 1, wherein the stereochemistry at the 7 and 9a position is cis or trans, and pharmaceutically acceptable salts thereof.

3. A compound according to the claim 2, wherein X is cyclopropyl, phenyl or 5-(10,11-dihydro-5H-dibenz(b,f) azepinyl); and $R_1$ is hydrogen or halogen, and pharmaceutically acceptable salts thereof.

4. A compound according to claim 3, wherein $R_1$ is fluoro; and

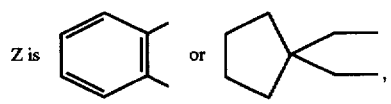

and pharmaceutically acceptable salts thereof.

5. A compound according to the claim 4, wherein $R_1$ is 4-fluoro; l is 0 to 3; and m, n and p are, each independently, 0 or 1, and pharmaceutically acceptable salts thereof.

6. A compound according to the claim 5, wherein X is cyclopropyl; Y is

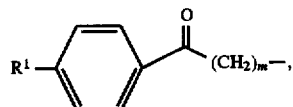

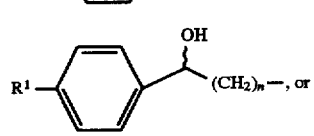

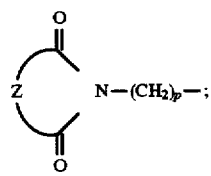

and l is 1, and pharmaceutically acceptable salts thereof.

7. A compound according to the claim 5, wherein X is phenyl; and l is 1 or 2, and pharmaceutically acceptable salts thereof.

8. A compound according to the claim 5, wherein X is 5-(10,11-dihydro-5H-dibenz(b,f)azepinyl); and l is 3, and pharmaceutically acceptable salts thereof.

9. A compound according to claim 1 selected from the group consisting of;

trans-7-[(p-fluorophenyl)hydroxymethyl]-2-(cyclopropylmethyl)perhydro-1H-pyrido[1,2-a]pyrazine;

cis-7-(p-fluorobenzoyl)-2-(cyclopropylmethyl)perhydro-1H-pyrido[1,2-a]pyrazine; trans-7-[(p-fluorophenyl)hydroxyethyl]-2-(phenylmethyl)perhydro-1H-pyrido[1,2-a]pyrazine;

trans-7-(p-fluorobenzoyl)-2-(benzyl)perhydro-1H-pyrido[1,2-a]pyrazine;

trans-7-[(p-fluorophenyl)hydroxymethyl]-2-(phenylethyl)perhydro-1H-pyrido [1,2-a]pyrazine;

cis-7-(cyclopentanespiro-3'-glutamidomethyl)-2-(2-phenylethyl)perhydro-1H-pyrido [1,2-a]pyrazine;

trans-7-(phtalimidomethyl)-2-(cyclopropylmethyl)perhydro-1H-pyrido[1,2-a]pyrazine;

cis-7-(phthalimidomethyl)-2-(phenyiethyl)perhydro-1H-pyrido[1,2-a]pyrazine;

trans-7-(p-fluorobenzoyl)-2-(cyclopropylmethyl)perhydro-1H-pyrido[1,2-a]pyrazine; and trans-7-(p-fluorobenzoyl)-2-(2-phenylethyl)perhydro-1H-pyrido[1,2-a]pyrazine; and pharmaceutically acceptable salts thereof.

10. A method of preventing or reducing chemical dependency by administering to a patient in need of such treatment an effective amount of a compound of claim 1.

11. A pharmaceutical composition for the treatment of psychotic disorders in a mammal which comprises a neuroleptic effective amount of a compound of claim 1 or a pharmaceutically acceptable salt thereof and a pharmaceutically acceptable carrier.

12. A method of treating psychotic disorders which comprises administering to a psychotic patient in need of such treatment an effective amount of a compound of claim 1 or a pharmaceutically acceptable salt thereof.

* * * * *